United States Patent
Ivancev

(10) Patent No.: US 9,474,641 B2
(45) Date of Patent: Oct. 25, 2016

(54) INDWELLING CATHETER ARRANGEMENT

(75) Inventor: Krasnodar Ivancev, Hampstead (GB)

(73) Assignee: Cook Medical Technologies LLC, Bloomington, IN (US)

( * ) Notice: Subject to any disclaimer, the term of this patent is extended or adjusted under 35 U.S.C. 154(b) by 852 days.

(21) Appl. No.: 12/287,395

(22) Filed: Oct. 9, 2008

(65) Prior Publication Data

US 2009/0105801 A1 Apr. 23, 2009

Related U.S. Application Data

(60) Provisional application No. 61/000,019, filed on Oct. 23, 2007.

(51) Int. Cl.
| | | |
|---|---|---|
| *A61F 2/06* | (2013.01) | |
| *A61F 2/966* | (2013.01) | |
| *A61F 2/954* | (2013.01) | |
| *A61F 2/07* | (2013.01) | |

(52) U.S. Cl.
CPC ............... *A61F 2/966* (2013.01); *A61F 2/954* (2013.01); *A61F 2/07* (2013.01); *A61F 2002/061* (2013.01)

(58) Field of Classification Search
CPC .................................. A61F 2/95–2/97; A61F 2002/9505–2002/9665; A61M 25/008; A61M 25/0067–25/0069; A61M 2025/0081
USPC .............. 606/108; 623/1.11, 1.12, 1.23, 1.35
See application file for complete search history.

(56) References Cited

U.S. PATENT DOCUMENTS

| | | | | |
|---|---|---|---|---|
| 4,983,169 A * | 1/1991 | Furukawa | ......... | A61M 25/0054 604/164.13 |
| 5,290,229 A | 3/1994 | Paskar | | |
| 5,470,315 A | 11/1995 | Adams | | |
| 5,601,539 A * | 2/1997 | Corso, Jr. | ..... | 604/524 |
| 5,718,861 A * | 2/1998 | Andrews | ............ | A61M 1/1072 264/235 |
| 5,775,327 A * | 7/1998 | Randolph | ......... | A61M 25/0054 600/374 |
| 5,976,120 A * | 11/1999 | Chow | ............... | A61M 25/0012 604/525 |
| 6,231,563 B1 * | 5/2001 | White et al. | .................. | 604/523 |
| 2004/0015151 A1 * | 1/2004 | Chambers | ..................... | 604/532 |
| 2004/0098084 A1 * | 5/2004 | Hartley et al. | ............... | 623/1.11 |
| 2004/0106974 A1 * | 6/2004 | Greenberg et al. | ......... | 623/1.11 |
| 2005/0149166 A1 * | 7/2005 | Schaeffer et al. | ............ | 623/1.13 |

(Continued)

FOREIGN PATENT DOCUMENTS

| | | |
|---|---|---|
| JP | 2001-526574 | 12/2001 |
| WO | WO 01/19425 A1 | 3/2001 |

(Continued)

OTHER PUBLICATIONS

Patent Examination Report No. 1 for corresponding AU 2008317435 dated Jan. 29, 2013, 5 pages.

(Continued)

*Primary Examiner* — Victor Nguyen
*Assistant Examiner* — Jonathan Hollm
(74) *Attorney, Agent, or Firm* — Brinks Gilson & Lione

(57) ABSTRACT

A stent graft delivery device (10) has an indwelling catheter (26) extending from a handle (12) through a pusher lumen and a stent graft lumen outside the guide wire catheter (32) of the delivery device towards the nose cone dilator (16). The indwelling catheter comprises a material able to transmit rotational and longitudinal movement (advancement and withdrawal) from the distal end to the proximal end thereof and a more flexible tip (24). The indwelling catheter facilitates catheterization of a branch artery.

12 Claims, 3 Drawing Sheets

(56) References Cited

U.S. PATENT DOCUMENTS

| | | | |
|---|---|---|---|
| 2006/0004433 A1* | 1/2006 | Greenberg et al. | 623/1.11 |
| 2006/0069323 A1* | 3/2006 | Elkins et al. | 600/585 |
| 2006/0149350 A1* | 7/2006 | Patel et al. | 623/1.11 |
| 2007/0060911 A1 | 3/2007 | Webster et al. | |
| 2007/0123910 A1 | 5/2007 | Hartley et al. | |
| 2008/0300666 A1* | 12/2008 | Heidner et al. | 623/1.11 |

FOREIGN PATENT DOCUMENTS

| | | |
|---|---|---|
| WO | WO 2004/089249 A1 | 10/2004 |
| WO | WO 2005/046526 | 5/2005 |
| WO | WO 2006/107919 A1 | 10/2006 |
| WO | WO 2007/059280 A1 | 5/2007 |
| WO | PCT/US2008/012017 | 2/2009 |

OTHER PUBLICATIONS

Communication for corresponding EP 08843042.6 dated Nov. 2, 2013, 2 pages.
Japanese Office Action for corresponding JP 2010-531028 dated Nov. 27, 2012 and English translation, 13 pages.
International Search Report and Written Opinion for corresponding PCT/US2008/012017 dated Feb. 19, 2009, 13 pages.
International Preliminary Report on Patentability for corresponding PCT/US2008/012017 dated Apr. 22, 2010, 10 pages.

* cited by examiner

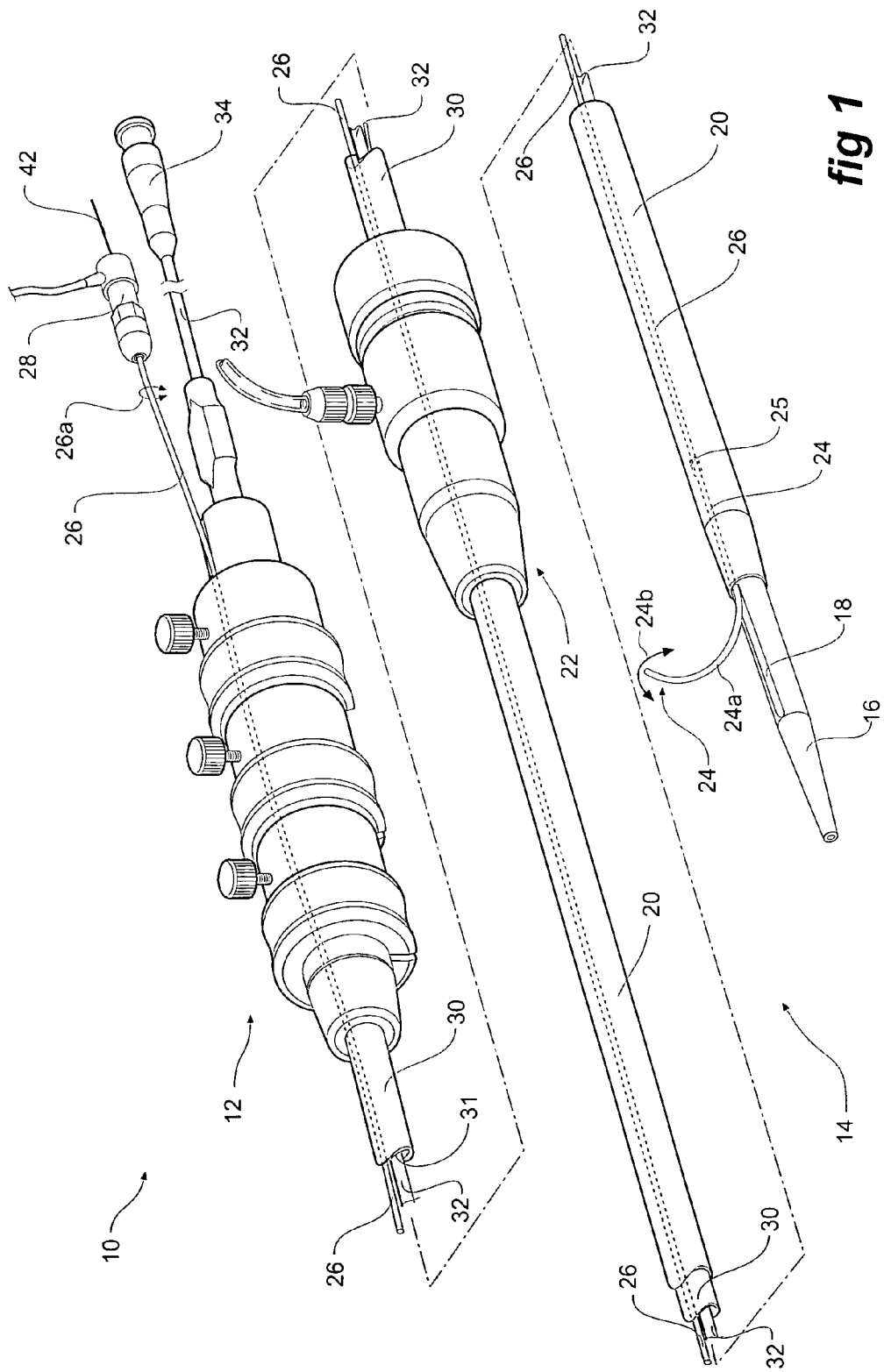

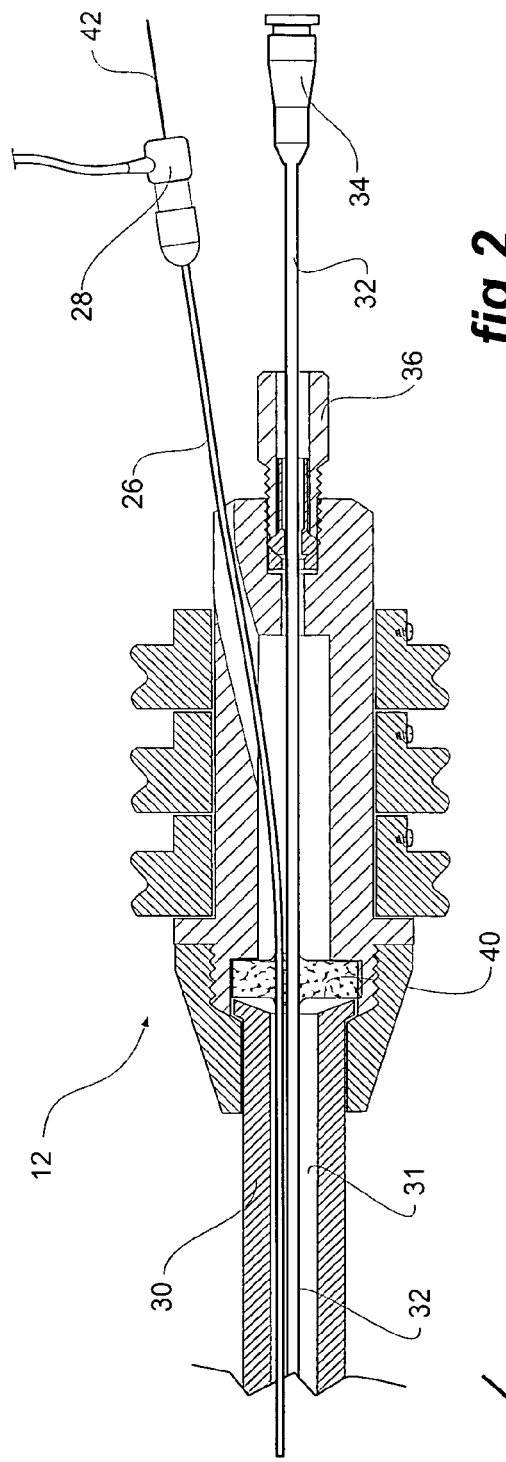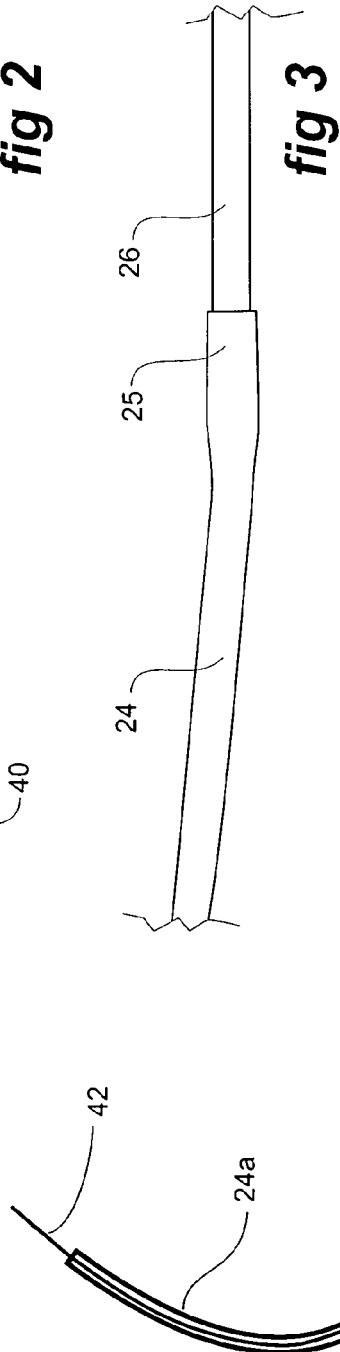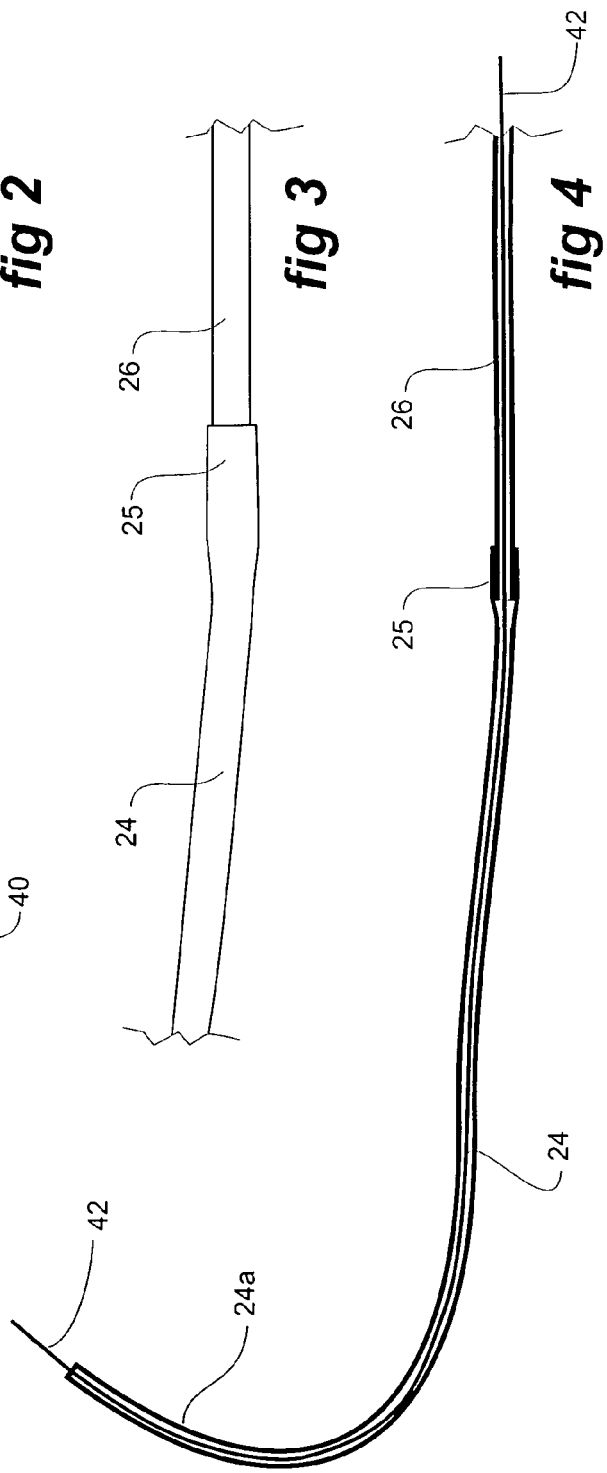

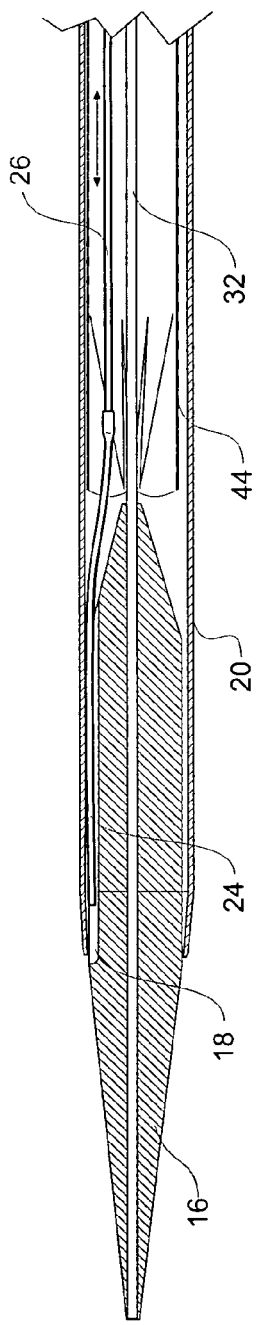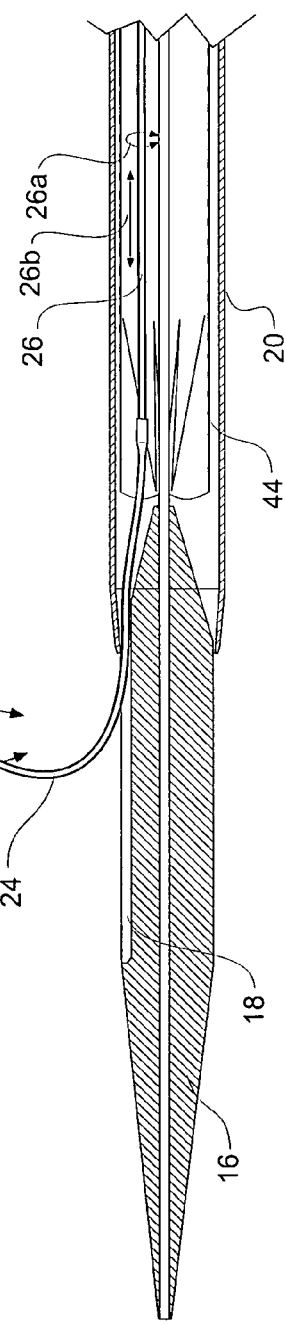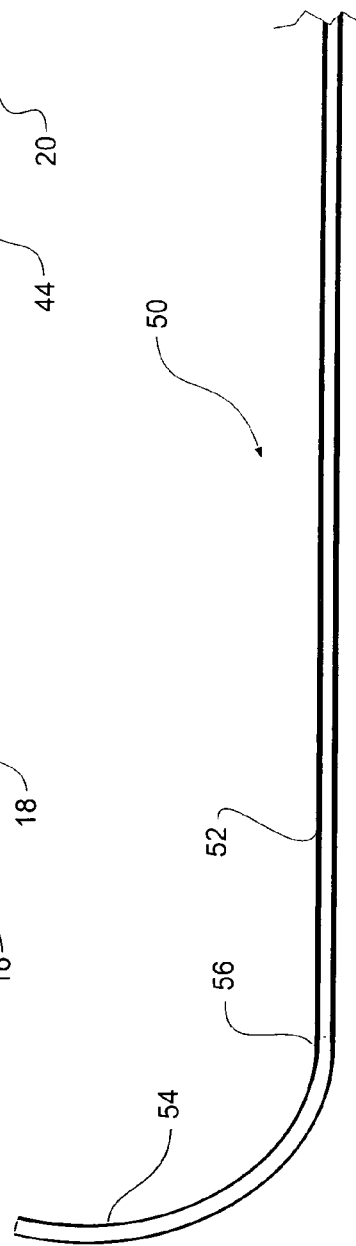

INDWELLING CATHETER ARRANGEMENT

CROSS-REFERENCE TO RELATED APPLICATIONS

This application claims priority of provisional application Ser. No. 61/000,019, filed Oct. 23, 2007.

TECHNICAL FIELD

This invention relates to a device for delivery of a stent graft into the human or animal vasculature by endovascular techniques and more particularly to an arrangement by which better control of delivery can be achieved.

BACKGROUND OF THE INVENTION

This invention will be generally discussed in relation to deployment of a stent graft where it is desirable to catheterize a side branch from a main vessel such as to catheterize an iliac artery from a contralateral iliac artery but it is to be understood that the invention is not so limited and may relate to any body lumen in which such a deployment is required. It may, for instance, be used for catheterization of one of the great vessels of the thoracic arch or the renal arteries.

Throughout this specification the term distal with respect to a portion of the aorta, a deployment device or a stent graft means the end of the aorta, deployment device or stent graft further away in the direction of blood flow away from the heart and the term proximal means the portion of the aorta, deployment device or end of the stent graft nearer to the heart. When applied to other vessels similar terms such as caudal and cranial should be understood.

Stent grafts are used for treatment of vasculature in the human or animal body to bypass a repair or defect in the vasculature. For instance, a stent graft may be used to span an aneurism which has occurred in or associated with the iliac artery. In many cases, however, such a damaged or defective portion of the vasculature may include a branch vessel such as an internal iliac artery. Bypassing such a branch vessel without providing blood flow into it can cause problems and hence it has been proposed to provide a side branch or fenestration on a stent graft which when deployed is positioned over the opening to the side vessel and then another stent graft can be deployed through the side branch or fenestration into the side vessel to provide a blood flow path to the side vessel from the stent graft.

There have been proposals, for instance, to deploy a branched stent graft into the common iliac artery via a femoral artery from a femoral incision using the Seldinger technique. Such a branched stent graft has a side arm which is placed to extend into or at least adjacent the internal iliac artery and then a leg extension can be placed through the side arm into the internal iliac artery, however, the use of such devices is very dependent upon favorable layout of the arteries and the ability to obtain access over the aortic bifurcation and in many cases, access is extremely difficult.

It has been proposed to use an indwelling auxiliary catheter positioned in the introducer. To do this it is necessary to snare a guide wire extended from the indwelling auxiliary catheter into or towards the contralateral iliac artery. Snaring can be a problem because of the nature of the prior art indwelling catheters. Prior art indwelling catheters have been constructed from a plastics material which cannot transfer rotational or longitudinal movement from one end to the other. In such a situation the position of the proximal end of the indwelling auxiliary catheter from which guide wire being snared is extended cannot be rotated or extended to direct the auxiliary guide wire in a selected direction and hence the guide wire can become entangled around the nose cone of the introducer or the guide wire of the introducer. This can be a particular problem in the thoracic arch because the great vessels extend off the thoracic arch at a range of angles and it is difficult to rotate the delivery device accurately so high up in the vasculature from the entry point in the groin (for instance).

This invention proposes an alternative method for enabling access for snaring of an indwelling auxiliary guide wire and a deployment device to enable such a method to be practiced.

It is the object of this invention therefore to provide an improved deployment device or at least to provide a physician with a useful alternative.

SUMMARY OF THE INVENTION

In one form therefore the invention comprises a stent graft delivery device comprising a handle at a distal end, a nose cone dilator at a proximal end, the nose cone dilator including a distal end, a guide wire catheter extending from the handle to and through the nose cone dilator at the proximal end, a pusher catheter extending from the handle towards the proximal end of the delivery device, a stent graft retained on the delivery device between the distal end of the nose cone dilator and the pusher catheter, the stent graft having a graft lumen therethrough and the guide wire catheter extending through the graft lumen, a pusher lumen through the pusher catheter, the guide wire catheter extending through the pusher lumen and able to move longitudinally and rotationally with respect to the pusher, an indwelling catheter extending from the handle through the pusher lumen and the stent graft lumen outside the guide wire catheter towards the nose cone dilator, the indwelling catheter comprising a distal end adjacent the handle and a proximal end adjacent the nose cone dilator, the indwelling catheter being formed from a material able to transmit rotational and longitudinal movement (advancement and withdrawal) from the distal end to the proximal end thereof.

Preferably the indwelling catheter is formed from a material which is both flexible and resilient but able to transmit the rotational and longitudinal movement (advancement and withdrawal) from the distal end to the proximal end thereof as discussed above.

The indwelling catheter can comprise a material selected from Nitinol™, a nickel titanium alloy, or stainless steel. The indwelling catheter can have a diameter of from 1.2185 mm to 1.2195 mm and a wall thickness of from 0.12275 mm to 0.12125 mm.

Preferably the indwelling catheter comprises a more flexible proximal tip, the proximal tip being pre-formed into a curved shape.

The more flexible proximal tip of the indwelling catheter can be formed from a biocompatible plastics material selected from polyurethane and PTFE.

The more flexible proximal tip when formed from polyurethane or PTFE can have a length of from 2 to 10 cm, a diameter of from 1.455 mm to 1.445 mm and a wall thickness of from 0.235 mm to 0.225 mm.

Alternatively the more flexible proximal tip can comprise the same material as the main part of the indwelling catheter and there may be a wall thickness transition between the more flexible proximal tip and the main part of the indwelling catheter to give the more flexible tip. The more flexible proximal tip can have a preformed curve heat set into it so that after it is released from the groove in the nose cone dilator sheath as discussed below it will regain its curved shape.

The Nitinol™ or stainless steel indwelling catheter can have a diameter for its entire length of from 1.2 mm to 1.3 mm and a wall thickness along a majority of its length of from 0.13 mm to 0.14 mm and in the tip portion a wall thickness of from 0.10 mm to 0.12 mm.

The nose cone dilator can comprise a longitudinal groove on its outer surface and the proximal end of the indwelling catheter can be received in the longitudinal groove.

There can be further included a sheath extending to the nose cone dilator and the sheath retaining the indwelling catheter in the longitudinal groove and retraction of the sheath allowing the proximal tip to regain its curved shape.

The distal end of the indwelling catheter can comprise a haemostatic seal.

In an alternative form the invention comprises a stent graft delivery device comprising a handle at a distal end, a nose cone dilator at a proximal end, the nose cone dilator including a distal end, a guide wire catheter extending from the handle to and through the nose cone dilator at the proximal end, a pusher catheter extending from the handle towards the proximal end of the delivery device, a stent graft retained on the delivery device between the distal end of the nose cone dilator and the pusher catheter, the stent graft having a graft lumen therethrough and the guide wire catheter extending through the graft lumen, a pusher lumen through the pusher catheter, the guide wire catheter extending through the pusher lumen and able to move longitudinally and rotationally with respect to the pusher, an indwelling catheter extending from the handle through the pusher lumen and the stent graft lumen outside the guide wire catheter towards the nose cone dilator, the indwelling catheter comprising a distal end adjacent the handle and a proximal end adjacent the nose cone dilator, the indwelling catheter comprising a main portion being a Nitinol hypotube and a proximal tip portion formed from a more flexible polyurethane tube, the proximal tip portion comprising a pre-formed curve whereby the indwelling catheter is able to transmit rotational and longitudinal movement (advancement and withdrawal) from the distal end to the proximal end thereof.

Preferably the nose cone dilator includes an outer surface and the nose cone dilator comprises a longitudinal groove on the outer surface and the flexible proximal end of the indwelling catheter is received in the longitudinal groove and thereby straightens out the pre-formed curve.

There may be further included a sheath extending to the nose cone dilator, wherein the sheath retains the indwelling catheter in the longitudinal groove during introduction of the delivery device and retraction of the sheath allows the proximal tip to regain its pre-curved shape.

It will be seen that by this invention an introducer device is provided in which the indwelling catheter can be controlled in its rotational position with respect to the delivery device so that a guide wire extending through the indwelling catheter can be snared from a side arm or a branch vessel from a main vessel and can then be catheterized. This is achieved by forming the indwelling catheter from a material which enables rotational forces to be transmitted along the full length of the indwelling catheter to its proximal end where a flexible tip can be rotated by action from outside the patient to direct the tip of the indwelling catheter towards the side vessel. The tip has preferably a pre-formed curve. Retraction or the sheath or advancement of the indwelling catheter from the sheath and rotation can enable accurate deployment of the indwelling guide wire.

BRIEF DESCRIPTION OF THE DRAWING

This then generally describes the invention but to assist with understanding reference will now be made to the accompanying drawings which show a preferred embodiment of the invention.

In the drawings:

FIG. 1 shows an introducer device incorporating an auxiliary catheter according to one embodiment of the present invention;

FIG. 2 shows detail of the handle portion of the delivery device shown in FIG. 1;

FIG. 3 shows detail of the connection between one portion of the indwelling catheter and its tip portion;

FIG. 4 shows detail of the proximal end of the indwelling catheter;

FIGS. 5 and 6 show various stages of deployment of the indwelling catheter at the proximal end of a stent graft delivery device; and FIG. 7 shows an alternative embodiment of indwelling catheter according to the present invention.

DETAILED DESCRIPTION

Now looking more closely at the drawings it will be seen that the delivery device 10 includes a handle portion 12 and a portion 14 which is deployed into a patient during the endovascular procedure. The portion to be entered in the patient comprises a nose cone dilator 16 with a longitudinal groove 18 on its outer surface. A sheath 20 extends from a sheath hub 22 to the nose cone dilator 16. As shown in FIG. 1 the sheath 20 has been partially retracted by retraction of the hub 22 to show a curved tip 24 of an indwelling catheter 26. The indwelling catheter 26 is formed partially from a Nitinol hypotube and extends from the curved tip 24 to a haemostatic seal 28 adjacent to the handle 12 of the delivery device 10. The curved tip 24 is formed from a softer more flexible material which preferably will retain a set curvature as discussed below in relation to FIG. 4. The indwelling catheter extends through a hemostatic seal 40 in the handle and the lumen 31 of the pusher 30.

The pusher 30 extends from the handle 12 through the hub 22 and terminates distally of the nose cone dilator 16. A guide wire catheter 32 extends from a syringe hub 34 through a pin vice 36 at the rear of the handle 12 through the lumen 31 of the pusher 30 to the nose cone dilator 16.

As can also be seen in detail in FIGS. 3 and 4 the indwelling catheter 26 includes a more rigid portion of tube 26 which is flexible and resilient and can transfer rotational and longitudinal movement and a tip portion 24 connected at a connection 25. In this embodiment the portion 26 is formed from Nitinol and the tip portion 24 is formed from polyurethane and preferably a radiopaque polyurethane so that the position of the curved tip 24 can be visualized. The connection 25 is shown as a push fit but can be any other convenient form of connection. The tip portion 24 has a pre-formed curve 24a which can be straightened out by being engaged under the sheath 20 but will resume its curved shape when released from the sheath 20. When straightened out by the sheath 20 the curved portion 24a of the tip portion 24 is received in the longitudinal groove 18 (see FIG. 1).

The main portion of the indwelling catheter of the present invention is flexible so that it can track through the vasculature of a patient along with the delivery device but sufficiently rigid such that it can transfer rotation or longitudinal pushing and pulling. The tip portion is flexible so that it can be straightened out to be received in the groove in the outer surface of the nose cone dilator but sufficiently rigid that it can be rotated to enable direction of the pre-formed curved tip as desired by a physician during an endovascular operation. Both portions are hollow so that an auxiliary guide wire can be deployed through them.

Along the length of the delivery device the auxiliary catheter 26 extends through a lumen 38 in the pusher 24 and in the handle extends through a haemostatic seal 40 and then extends out of the rear of the handle. An auxiliary guide wire 42 extends through the indwelling catheter 26 and can be manipulated to extend out of the proximal end of the auxiliary catheter.

FIGS. 5 and 6 show the proximal end of a delivery device according to one embodiment of the present invention.

In FIG. 5 a cross-sectional view is shown of the proximal end of the introducer device. In this embodiment the sheath 20 is advanced to cover the stent graft 44 which is retained around the guide wire catheter 32 just distal of the nose cone dilator 16. The more flexible tip portion 24 of the indwelling catheter 26 is received in the longitudinal groove 18 in the nose cone dilator 16 and the curved portion has been straightened out to lie flat in the groove 18. The indwelling catheter 26 extends through the lumen of the stent graft 44.

As shown in FIG. 6 the sheath 20 has been retracted so that it still covers the stent graft 44 but has released the curved tip end 24a of the tip portion 24 of the indwelling catheter 26 so that it has regained its original curved shape. At this stage rotation of the indwelling catheter 26 by gripping and rotating the haemostatic seal 28 (see FIG. 1) will transfer the rotation as indicated by arrow 26a along the length of the delivery device due to the more rigid nature of the Nitinol portion of the indwelling catheter and this will cause the tip to rotate, as shown by arrow 24b, enabling the end of the indwelling catheter to more accurately aimed at a side vessel such that the indwelling guide wire 42 can be extended to catheterize the side vessel. Similarly the rigid nature of the Nitinol portion of the indwelling catheter enables longitudinal movement (advancement and withdrawal) of the indwelling catheter 26 as shown by the arrow 26b. This enables fine positioning of the curved tip longitudinally in the vasculature of a patient without a physician having to move then entire delivery device.

FIG. 7 shows an alternative embodiment of indwelling catheter according to the present invention. In this embodiment the indwelling catheter 50 includes a more rigid portion of tube 52 which is flexible and resilient and can transfer rotational and longitudinal movement and a tip portion 54. In this embodiment the entire indwelling catheter is formed from Nitinol™ or stainless steel. The tip portion 54 is formed with a lesser wall thickness produced by a wall thickness transition at 56. The tip portion 54 has a pre-formed curve which can be straightened out by being engaged under the sheath 20 (see FIG. 5, for instance) but will resume its curved shape when released from the sheath 20. When straightened out by the sheath 20 the curved portion 56 is received in the longitudinal groove 18 on the outer surface of the nose cone dilator (see FIG. 5).

In this embodiment the indwelling catheter can have a diameter for its entire length of from 1.2 mm to 1.3 mm and a wall thickness along a majority of its length of from 0.13 mm to 0.14 mm and in the tip portion a wall thickness of from 0.10 mm to 0.12 mm.

Throughout this specification various indications have been given as to the scope of the invention but the invention is not limited to any one of these but may reside in two or more of these combined together. The examples are given for illustration only and not for limitation.

What is claimed is:

1. A stent graft delivery device comprising a handle at a distal end, a nose cone dilator at a proximal end, the nose cone dilator including a distal end,
   a guide wire catheter extending from the handle to and through the nose cone dilator at the proximal end,
   a pusher catheter extending from the handle towards the proximal end of the delivery device,
   a stent graft retained on the delivery device between the distal end of the nose cone dilator and the pusher catheter, the stent graft having a graft lumen therethrough and the guide wire catheter extending through the graft lumen,
   a pusher lumen through the pusher catheter, the guide wire catheter extending through the pusher lumen and longitudinally and rotationally movable with respect to the pusher catheter,
   an indwelling catheter extending from the handle through the pusher lumen and the stent graft lumen outside the guide wire catheter towards the nose cone dilator, the indwelling catheter comprising a distal end adjacent the handle, a proximal end adjacent the nose cone dilator, a flexible proximal tip, and a main portion comprising a metal hypotube that is both flexible and resilient,
   wherein the indwelling catheter is of sufficient rigidity such that it is configured to transmit rotational movement along the full length of the indwelling catheter from its distal end to its proximal end and to the flexible proximal tip such that rotation of the distal end of the catheter from outside the patient translates into rotation of the flexible proximal tip, and wherein the indwelling catheter is configured to transmit, longitudinal advancement and longitudinal withdrawal from the distal end to the proximal end thereof;
   the flexible proximal tip having a pre-formed continuous semi-circular curved shape; wherein the indwelling catheter immediately distal to the flexible proximal tip is less flexible than the proximal tip;
   wherein the flexible proximal tip retains its pre-formed curve with an indwelling guidewire disposed through the pre-formed curve and throughout the length of the indwelling guidewire such that the indwelling guidewire is extended through the curve and can be extended into a targeted branch vessel, and
   wherein an inner diameter of the flexible proximal tip is greater than an inner diameter of the main portion.

2. The stent graft delivery device as in claim 1 wherein the flexible proximal tip of the indwelling catheter is formed from a biocompatible plastics material selected from polyurethane and PTFE.

3. The stent graft delivery device as in claim 1 wherein the flexible proximal tip has a length of from 2 to 10 cm.

4. The stent graft delivery device as in claim 1 wherein the nose cone dilator includes an outer surface and the nose cone dilator comprises a longitudinal groove on the outer surface and the proximal end of the indwelling catheter is received in the longitudinal groove.

5. The stent graft delivery device as in claim 4 further including a sheath extending to the nose cone dilator and the sheath retains the indwelling catheter in the longitudinal groove and retraction of the sheath allows the proximal tip to regain its curved shape.

6. The stent graft delivery device as in claim 1 wherein the indwelling catheter comprises a diameter of from 1.2185 mm to 1.2195 mm and a wall thickness of from 0.12275 mm to 0.12125 mm.

7. The stent graft delivery device as in claim 1 wherein the distal end of the indwelling catheter includes a haemostatic seal.

8. The stent graft delivery device as in claim 1 wherein the flexible proximal tip of the indwelling catheter comprises the same material as the indwelling catheter and comprising a wall thickness transition between the flexible proximal tip and the indwelling catheter and a smaller wall thickness in the flexible proximal tip.

9. The stent graft delivery device as in claim 8, wherein the indwelling catheter comprises a diameter for its entire length of from 1.2 mm to 1.3 mm and a wall thickness along a majority of its length of from 0.13 mm to 0.14 mm and the flexible tip comprising a wall thickness of from 0.10 mm to 0.12 mm.

10. The stent graft delivery device of claim 1 wherein the preformed radiused curve is a single continuous curve.

11. The stent graft delivery device of claim 10, wherein the single continuous curve is greater than 90 degrees.

12. The stent graft delivery device of claim 10 wherein the most proximal tip of the single continuous curve points toward the distal end of the delivery system.

* * * * *